United States Patent [19]

Vanderbilt et al.

[11] 4,256,888

[45] Mar. 17, 1981

[54] PREPARATION OF 2-CHLOROPYRIMIDINES

[75] Inventors: Jeffrey J. Vanderbilt; William C. Gose; James P. Cleveland, all of Kingsport, Tenn.

[73] Assignee: Eastman Kodak Company, Rochester, N.Y.

[21] Appl. No.: 134,044

[22] Filed: Mar. 26, 1980

[51] Int. Cl.³ .............................................. C07D 239/30
[52] U.S. Cl. ...................................................... 544/334
[58] Field of Search ............................................ 544/334

[56] References Cited

U.S. PATENT DOCUMENTS 3,108,104 10/1963 Seefelder et al. ..................... 544/334

OTHER PUBLICATIONS

Roblin et al., J. Art. 72, 4890–4892, (1950).

Primary Examiner—Nicholas S. Rizzo
Attorney, Agent, or Firm—J. Frederick Thomsen; Daniel B. Reece III

[57] ABSTRACT

2-Chloropyrimidines are prepared by treating 2-mercaptopyrimidines with chlorine or sulfuryl chloride in the presence of one or more $C_2$–$C_4$ carboxylic acids and in the absence of significant amounts of water.

3 Claims, No Drawings

PREPARATION OF 2-CHLOROPYRIMIDINES

This invention relates to a novel process for the synthesis of 2-chloropyrimidines.

It is known (*J. Am. Chem. Soc.*, 72, 4890) that when various mercaptoheterocycles, including certain 2-mercaptopyrimidines, are treated with chlorine in the presence of dilute hydrochloric or acetic acid, the product obtained is the corresponding chlorosulfonyl compound. The cited reference also discloses that the chlorosulfonylpyrimidines prepared were obtained in poor to fair yields and that they decompose to chloropyrimidines upon standing at room temperature.

We have discovered that 2-chloropyrimidines can be obtained in relatively good yields by treating 2-mercaptopyrimidines with chlorine or sulfuryl chloride in the presence of one or more $C_2$–$C_4$ carboxylic acids and in the absence of significant amounts of water. The 2-chloropyrimidines are useful intermediates for the preparation of physiologically active compounds such as those described in U.S. Pat. No. 3,717,634.

The 2-mercaptopyrimidines which can be used in the process of our invention include 2-mercaptopyrimidine which can be substituted with inert substituents such as alkyl and alkoxy and the hydrochloride salts of such compounds. Representative of the 2-mercaptopyrimidines are those having the general formula

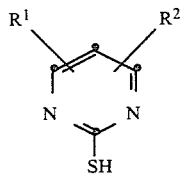

wherein $R^1$ and $R^2$ are independently selected from hydrogen, $C_1$–$C_4$ alkyl and $C_1$–$C_4$ alkoxy and the hydrochloride salts of such compounds. Since copious amounts of hydrochloric acid are formed during the practice of the process, the 2-chloropyrimidine formed is the hydrochloride salt.

The amount of chlorinating agent (chlorine or sulfuryl chloride) that should be used is at least 3 and up to 5 moles per mole of the mercaptopyrimidine reactant. The reaction should be carried out at a temperature less than 15° C. to avoid side reactions. The preferred temperature is in the range of about $-5°$ to 5° C.

The theoretical amount of carboxylic acid that is required in the practice of the process is 2 moles of acid per mole of 2-mercaptopyrimidine. However, in actual practice of the ratio can be substantially greater. For example when the reaction medium consists primarily of a carboxylic acid, the amount used must be sufficient to give a workable reaction mixture. It is apparent that acetic acid cannot be used as the only component of the reaction medium since it freezes at about 16.6° C. and thus it must be used in combination with a $C_3$ or $C_4$ acid when no other solvent is employed. We have found that the use of an inert solvent is advantageous in recovering the 2-chloropyrimidine. Examples of such solvents include those commonly used in chlorination reactions such as chlorinated hydrocarbons. Specific examples include dichloromethane, chloroform, carbon tectrachloride, dichloroethane, dichloropropane. When an inert solvent is used the mole ratio of acid to reactant usually is in the range of about 2 to 1. The amount of inert solvent is dictated primarily by economic consideration such as the cost of the solvent and its recovery and the efficient use of equipment.

The amount of water present during the practice of our novel process should not exceed 2 moles per mole of the 2-mercaptopyrimidine reactant. Although it usually is not practical to do so, the process can be performed under absolutely anhydrous conditions.

The novel process of our invention is further illustrated by the following example.

2-CHLOROPYRIMIDINE HYDROCHLORIDE

A 300 ml. three-necked, round-bottomed flask, cooled to 0° with a constant temperature circulating bath, was charged with 200 ml. of dichloromethane, 20.00 g. (0.178 mole) of 2-mercaptopyrimidine and 20.00 g. (0.33 mole) of glacial acetic acid. The heterogeneous slurry was stirred and 37.9 g. (0.53 mole) chlorine was added sub-surfacely over the course of about 9 hours at 0°. The excess chlorine was purged from the system with nitrogen and the dichloromethane was allowed to evaporate by standing at room temperature leaving 27.00 g. of crude 2-chloropyrimidine hydrochloride, a white solid.

The invention has been described in detail with particular reference to certain preferred embodiments thereof, but it will be understood that variations and modifications can be effected within the spirit and scope of the invention.

We claim:

1. Process for the preparation of a 2-chloropyrimidine hydrochloride which comprises treating a 2-mercaptopyrimidine or its hydrochloride with chlorine or sulfuryl chloride in the presence of one or more $C_2$–$C_4$ carboxylic acids and in the presence of not more than 2 moles of water per mole of the 2-mercaptopyrimidine reactant.

2. Process for the preparation of a 2-chloropyrimidine hydrochloride having the formula

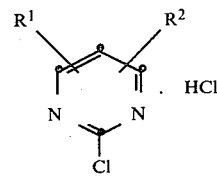

which comprises treating the corresponding 2-mercaptopyrimidine or its hyrochloride salt with chlorine at about $-5°$ to 15° C. in the presence of a $C_2$–$C_4$ carboxylic acid and an inert chlorinated hydrocarbon and in the presence of not more than 2 moles of water per mole of the 2-mercaptopyrimidines reactant.

3. Process of claim 2 wherein the chlorine used is at least 3 moles per mole of 2-mercaptopyrimidine reactant and the temperature is about $-5°$ to 5° C.

* * * * *